United States Patent [19]

Brown

[11] Patent Number: 5,396,672
[45] Date of Patent: Mar. 14, 1995

[54] COMBINATION SURGICAL TABLE AND PROTECTIVE COVER AND METHOD THEREFOR

[76] Inventor: Timothy E. Brown, 107 E. McKinley, Tempe, Ariz. 85281

[21] Appl. No.: 137,723

[22] Filed: Oct. 18, 1993

[51] Int. Cl.6 .................. A47G 9/04; A61G 13/00
[52] U.S. Cl. .................................. 5/600; 5/484; 5/923
[58] Field of Search .............. 5/600, 482, 484, 922, 5/923, 496, 498, 606

[56] References Cited

U.S. PATENT DOCUMENTS

| | | | |
|---|---|---|---|
| 4,910,819 | 3/1990 | Brown | 5/484 |
| 4,991,242 | 2/1991 | Brown | 5/600 |
| 5,070,520 | 12/1991 | Brown | 5/484 |
| 5,081,729 | 1/1992 | Menday | 5/484 |
| 5,133,097 | 7/1992 | Pyles | 5/482 |
| 5,208,926 | 5/1993 | Stackhouse | 5/482 |

Primary Examiner—Alexander Grosz
Attorney, Agent, or Firm—Harry M. Weiss

[57] ABSTRACT

A combination surgical table and protective cover is disclosed in which a surgical table is provided with one or more cushions for supporting a patient. A protective cover is coupled to each cushion and to the surgical table, thereby minimizing surface contamination of each cushion and the table. Each protective cover has a connecting portion which couples the protective cover to both the surgical table and to each cushion. A shielding section has a general shape which is substantially equivalent to the shape of each cushion for shielding each cushion and the table from the contamination. Flow guides are coupled to the shielding section for directing contamination away from each cushion and away from the surgical table.

20 Claims, 3 Drawing Sheets

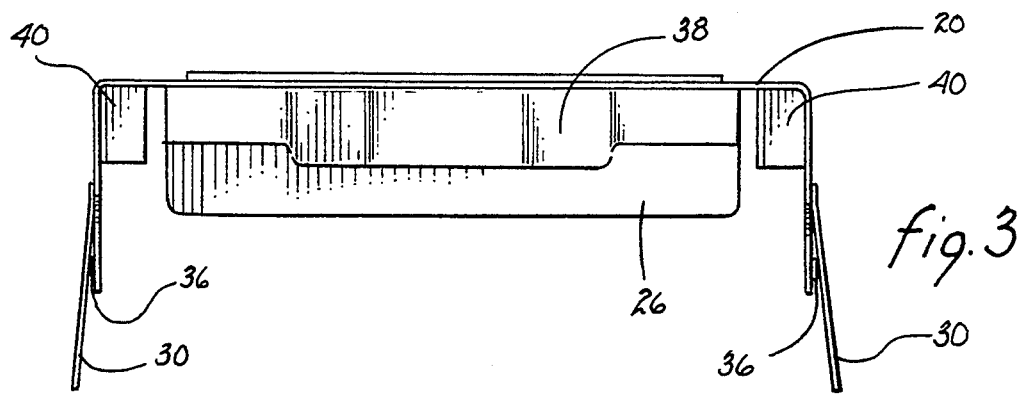
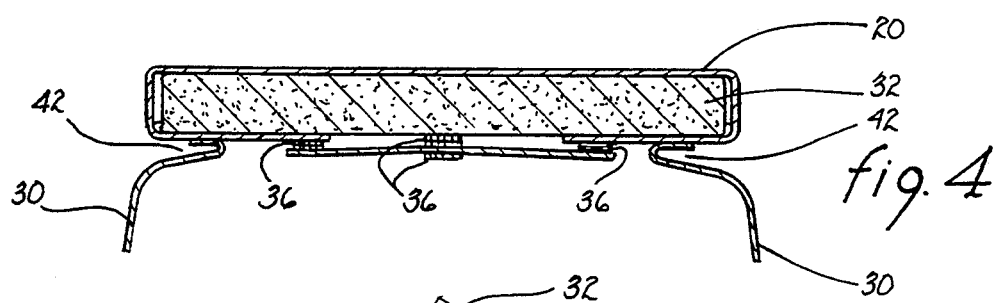
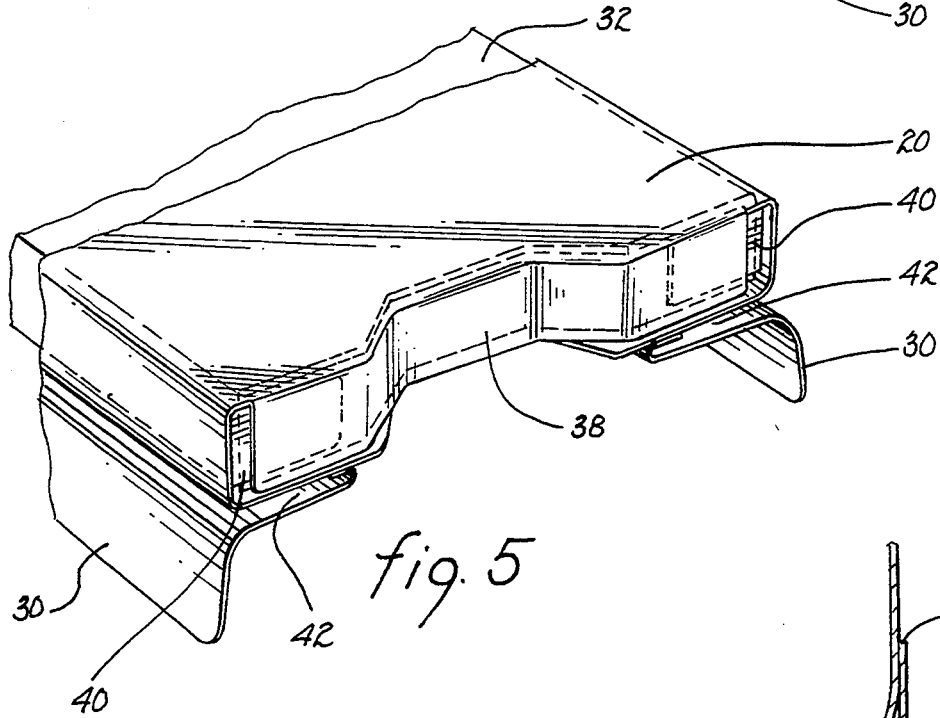
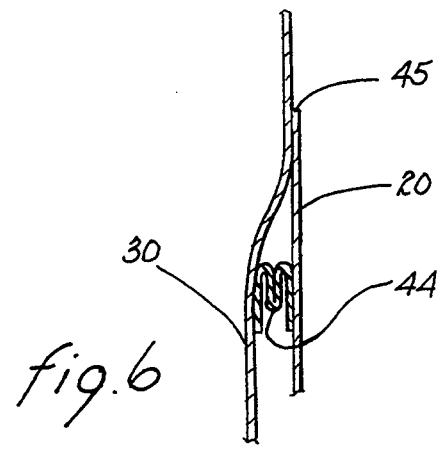

COMBINATION SURGICAL TABLE AND PROTECTIVE COVER AND METHOD THEREFOR

FIELD OF THE INVENTION

This invention relates generally to surgical tables and, more specifically, to a surgical table protective cover and method therefor which provides shielding for the surgical table which directs the flow of potential contaminants away from both the surgical table and the surgical table cushion or cushions, thereby reducing the amount of time required to properly clean the surgical table and its associated cushions.

DESCRIPTION OF THE PRIOR ART

The surgical table is a heavily utilized piece of hospital equipment that is used in a large number of medical procedures. These procedures vary in complexity from relatively simple outpatient cases to more complex level-one trauma cases.

There are a variety of different types of surgical tables utilized for distinct purposes such as for general surgery, urological surgery, orthopedic surgery, and neurosurgery. In general, all of these surgical tables perform the same basic function, namely the supporting and the positioning of a patient for surgery. Most surgical tables are multi-functional and multi-configurational. In other words, in any given surgical procedure, the surgical table may have a section removed, attached, or positioned in order to provide proper patient support.

Most surgical tables are configured as either a single top or a double top variant. The single top configuration is provided with a radiotransluscent patient support surface which is supported by a metallic type framework and a base structure. The properties associated with a radiotransluscent surface allow the passage of X-ray beams in order to provide the capability to perform radiological procedures with the patient in place before, during, and after the surgical procedure. The double top configuration provides one table top mechanically supported above another table top. The upper table top, which is used as the patient support surface, is constructed of a radiotransluscent material. The lower of the two table tops is typically made from either a metallic or a radiotransluscent material. The lower table top usually functions as a platform upon which X-ray film cassettes may be placed under the patient in order to provide the capability to perform radiological procedures with the patient in place before, during, and after the surgical procedure. Both types of table tops are supported by a base structure.

Commonly, either table top configuration is comprised of a plurality of sections. In particular, one will usually find a central section that is permanently mounted on the table base support structure and one or more sections that are mechanically fixed to either end of the central section. Oftentimes, these affixed sections are hinged in a manner that allows them to be moved and subsequently clamped or locked into a required position.

Also found in either table top configuration is a notch or cut-out in one end of the center, or main, section cushion. This notch, known as a perineal cut-out, allows a standing or sitting surgeon to have maximum access in the vicinity of the lower torso of a patient.

Most surgical tables have cushions appropriately sized and shaped to fit the corresponding sections of the surgical table. The cushion and table top section usually have complementary VELCRO portions running lengthwise in order to fix each cushion to the appropriate table top section.

A patient arm rest which mechanically clamps to the side of either table top configuration is also commonly available. Each table top section has a rail mounted to each side which results in a collective rail that runs lengthwise along both sides of the table. The arm rest and/or other accessories typically clamp on to this rail.

These prior art surgical tables and their associated cushions and accessories are often subjected to a wide variety of bodily fluids, such as blood, vomit, and urine. In order to effectively remove such types of bodily contamination, surgical tables, along with their cushions and accessories are also subjected to harsh fluid cleansers and disinfectants. A major problem with the prior art surgical tables is that the aforementioned fluids and other potential sources of surface contamination frequently flow onto, around, and underneath the cushions, onto the table top portion, and down the base structure. Over a relatively short period of time, the surface contamination from these fluids collects in hard to clean areas of the surgical table and cushions. Worse yet, as the surgical table cushions begin to wear, these fluids are absorbed into the cushions. Some of these fluids, such as harsh fluid disinfectants and cleansers, tend to crack the plastic like covering of the cushions, thereby allowing further absorption of contaminants into the cushions which results in greater damage to the cushions.

Surgical tables and their associated cushions and accessories must be thoroughly cleaned after each use. It should be appreciated that due to the construction of these tables, it is extremely time consuming to properly clean a surgical table. Since a surgical table cannot be used for surgical procedures until it has been thoroughly cleaned, most hospitals spend a great amount of money for extra surgical tables and spare surgical table cushions so that clean tables are available even during periods in which a large number of surgical procedures are done over too short a period of time to allow for proper surgical table cleaning.

U.S. Pat. No. 4,910,819 which issued on Mar. 27, 1990 in the name of the Applicant of the subject patent application discloses a protective covering and method therefor to protect against spills on a cushion that rests on a baseplate of a CT-scanner table. U.S. Pat. No. 4,991,242 which issued on Feb. 12, 1991 in the name of the Applicant of the subject patent application discloses a protective covering and method therefor to protect against spills on a cushion that rests on an angiographic or cardiac catheterization machine table. U.S. Pat. No. 5,070,520 which issued on Dec. 3, 1991 in the name of the Applicant of the subject patent application discloses a fluid flow control contoured cushion and protective cover and method therefor which rests on an X-ray or a non-X-ray table assembly to protect against spills. However, the protective covers and methods of prior U.S. Pat. Nos. 4,910,819, 4,991,242, and 5,070,520 do not have protective covers that overcome the aforementioned described problems of having bodily fluids, disinfectant solutions, and other potential surface contaminants going onto and into a surgical table assembly having a base, a patient table comprising one or more segments, one or more cushions, and attachable accessories. Therefore, a need existed to provide an improved protective covering and method which a) permits the attachment of protective covers to one or more cushion sections that singly or collectively comprise a patient cushion, b) provides protective side flap portions which originate beneath the patient cushion to allow a tucking space for cloth patient sheets on opposite sides of the cover and cushion assembly, c) provides fluid flow protection in the perineal area, among others, by flaps and fluid flow blocks, and d) provides attachable protective covering sections for attachable patient arm rests and other attachable accessories of the patient table.

SUMMARY OF THE INVENTION

In accordance with one embodiment of this invention, it is an object of this invention to provide a combination surgical table and protective cover.

It is another object of this invention to provide a method of operating a combination surgical table and protective cover.

It is a further object of this invention to provide a combination surgical table and protective cover that minimizes the amount of surface contamination that collects on a surgical table and its associated cushions and accessories.

It is yet another object of this invention to provide a combination surgical table and protective cover that reduces the amount of time required for cleaning a surgical table.

BRIEF DESCRIPTION OF THE PREFERRED EMBODIMENTS

In accordance with one embodiment of this invention, a combination surgical table and protective cover means is disclosed comprising, in combination, a surgical table having at least one cushion for supporting a patient, and protective cover means coupled to the cushion and to the surgical table for minimizing surface contamination of the cushion and the table comprising, connecting means having a portion coupled to the table and having another portion coupled to the cushion for coupling the protective cover means to the cushion, shielding means having a first portion and a second portion both coupled to the connecting means and having a general shape substantially equivalent to a shape of the cushion for shielding the cushion and the table from the contamination, and flow guide means coupled to the shielding means for directing the contamination away from both the cushion and the table. In addition, each of the connecting means, the cushion, the table, and the shielding means includes VELCRO sealing means for coupling the connecting means to each of the table, the cushion, and the shielding means.

In accordance with another embodiment of this invention, a method of operating a combination surgical table and protective cover means is provided comprising the steps of providing a surgical table having at least one cushion for supporting a patient, and providing protective cover means coupled to the cushion and to the surgical table for minimizing surface contamination of the cushion and the table comprising the steps of providing connecting means having a portion coupled to the table and having another portion coupled to the cushion for coupling the protective cover means to the cushion, providing shielding means having a first portion and a second portion both coupled to the connecting means and having a general shape substantially equivalent to a shape of the cushion for shielding the cushion and the table from the contamination, and providing flow guide means coupled to the shielding means for directing the contamination away from both the cushion and the table. In addition, each of the connecting means, the cushion, the table, and the shielding means includes VELCRO sealing means for coupling the connecting means to each of the table, the cushion, and the shielding means.

The foregoing and other objects, features, and advantages of the invention will be apparent from the following, more particular, description of the preferred embodiments of the invention, as illustrated in the accompanying drawings.

BRIEF DESCRIPTION OF THE DRAWINGS

FIG. 3 is a cross sectional view of FIG. 2 taken along the line 3—3.

FIG. 4 is a cross sectional view of FIG. 1 taken along the line 4—4.

FIG. 5 is a perspective view showing a portion of the mid-section cushion and its associated protective cover in order to emphasize the perineal cut-out portion.

FIG. 6 is a cross sectional view of FIG. 2 taken along the line 6—6.

DESCRIPTION OF THE PREFERRED EMBODIMENT

Figure 1:
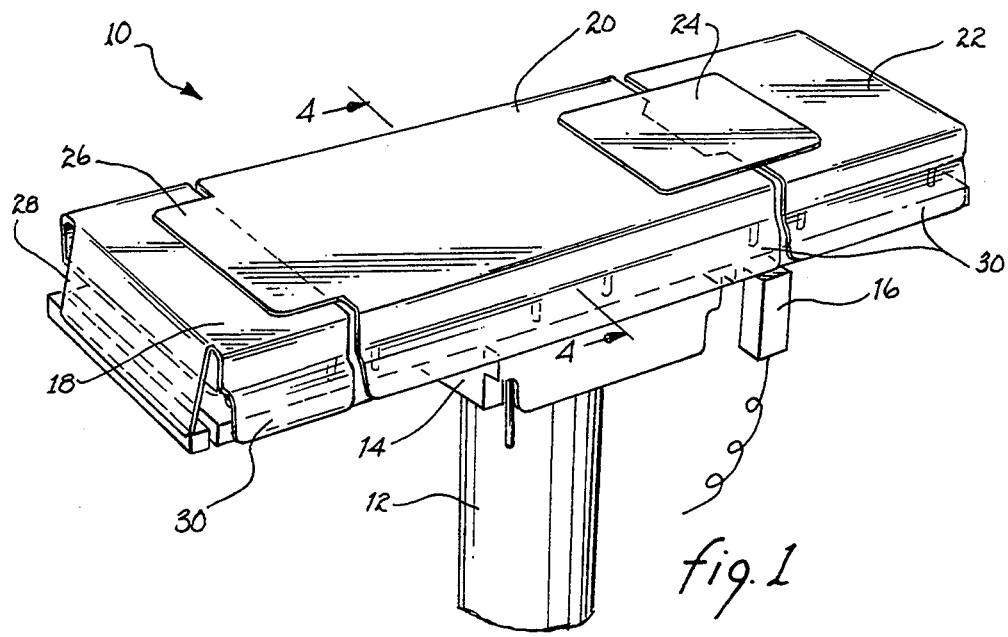
FIG. 1 is a perspective view of the combination surgical table and protective cover showing an embodiment providing a surgical table having a head cushion, a mid-section cushion, and a foot cushion.

Referring to FIG. 1, a combination surgical table and protective cover is shown and is generally designated by reference number 10. Note that the surgical table shown in FIG. 1 is only one of a number of different types of surgical tables that could use protective covers that are substantially similar to those shown in FIG. 1. The surgical table includes a base support 12, a patient table top 14, and an electronic controller 16 for controlling the operation of the surgical table. The surgical table top 14 supports a head cushion, a mid-section cushion, and a foot cushion that are covered by a head cushion protective cover 18, a mid-section cushion protective cover 20, and a foot cushion protective cover 22, respectively. Note that the mid-section cushion protective cover 20 has a perineal cut-out portion at the end adjacent to the foot cushion protective cover 22. The mid-section cushion protective cover 20 has a flap 24 that can be used in one position to cover the perineal cut-out, or alternatively, the flap 24 can be placed in another position to uncover the perineal cut-out in order to give optimum access to the patient during a perineal type procedure. The mid-section cushion protective cover 20 has another flap 26 that can be used in one position to cover the space between the mid-section cushion protective cover 20 and the head cushion protective cover 18. Note that the flap 26 can also be moved into another position to give easy access to this space between the mid-section cushion protective cover 20 and the head cushion protective cover 18. The head cushion protective cover 18 has a flap 28 that is shown hanging down from the cover 18. In general, any cushion protective cover on the end of the surgical table top 14 can have a flap similar to the flap 28 which is especially useful in directing fluids away from the table top 14. Also, any cushion protective cover located adjacent to another protective cover may have a flap analogous to either of flaps 24 or 26 which direct fluid flow away from the space in-between adjacent protective covers. Each of the protective covers 18, 20, and 22 have side flaps 30 that direct the flow of potential contaminants away from the surgical table top 14 and its associated cushions. The combined effect of the protective covers 18, 20, and 22, the flaps 24, 26, and 28, and the side flaps 30 is to minimize the surface contamination of the surgical table top 14 and its associated cushions.

Figure 2:
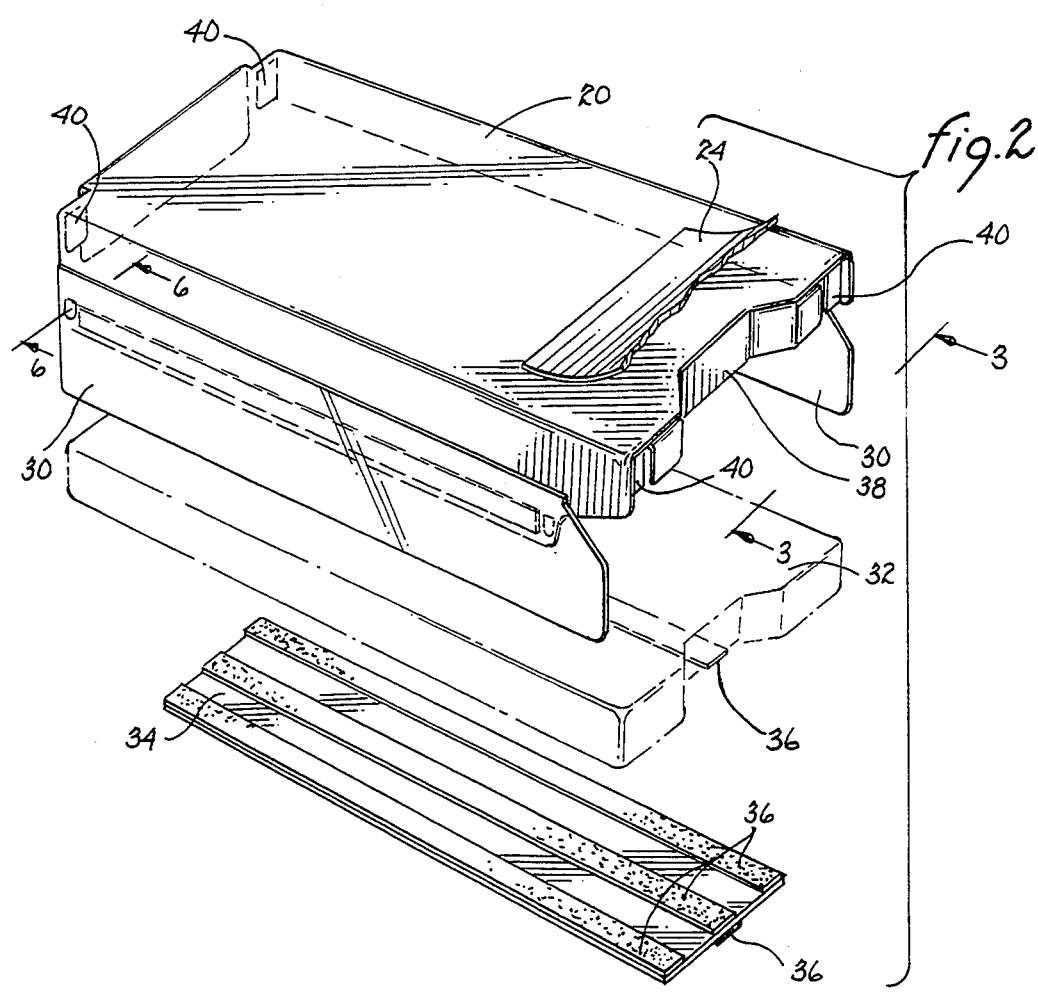
FIG. 2 is an exploded perspective view showing the mid-section cushion and its associated protective cover from FIG. 1.

Referring to FIGS. 2 and 3, the mid-section cushion 32 is shown to have a VELCRO sealing portion 36. The connecting portion 34 has a single VELCRO sealing portion 36 on one side that is for coupling to the VELCRO sealing portion 36 on the mid-section cushion 32. Three VELCRO sealing portions 36 are on the other side of the connecting portion 34. One of these three VELCRO sealing portions 36 that is centrally located is used for coupling to another VELCRO sealing portion 36 located on the table top 14 which is not shown for the sake of simplicity. The other two of these three VELCRO sealing portions 36 are used to couple the mid-section protective cover 20 to the mid-section cushion 32 via the connecting portion 34. Note that the mid-section protective cover 20 substantially conforms to the shape of the mid-section cushion 32 as do each of the protective covers with their respective cushions. Of particular interest, the mid-section protective cover 20 has a perineal cut-out guard 38 and corner guards 40 to keep any fluids that might happen to fall into the perineal cut-out region from contacting the cushion 32. Each of the other protective covers 18 and 22 have other guards that are similar in function to the perineal cut-out guard 38. In addition, each of the other protective covers 18 and 22 have corner guards 40 for protecting their respective cushions.

Referring to FIG. 4, the connecting portion 34 is shown coupled to the mid-section protective cover 20 and to the mid-section cushion 32. Note that the bottom, center VELCRO sealing portion 36 is the one used for coupling to the surgical table top 14. Of particular interest in FIGS. 4 and 5, note that when the protective cover 20 is coupled to the cushion 32 and to the connecting portion 34, a tucking portion 42 is created. In a similar manner, protective covers 18 and 22 also form a tucking portion 42, thereby creating a tucking portion 42 that runs lengthwise along the surgical table. Typically, a bed sheet is placed over the surgical table and is tucked into the tucking portions 42 so that the sheet is held in place by the weight of the cushion 32. Again, for the sake of simplicity, no bed sheet is shown in the tucking portions 42 of FIGS. 4 and 5.

Referring to FIG. 6, the mid-section protective cover 20 is coupled to the side flap portion 30 at a seam connection 45. An additional connection 44 is formed between the side flap 30 and the mid-section protective cover 20 in order to strengthen the holding power at this point. In a analogous manner, protective covers 18 and 22 also have additional connections 44 formed between their side flaps 30 the covers 18 and 22 themselves. The additional connections 44 are substantially strong and flexible like the protective covers themselves. The protective covers 18, 20, and 22 including the flaps 24, 26, 28, and 30, and the connection portions 34 are preferably made from 23 mil flexible vinyl sheets, however, other suitable materials may be used that are substantially strong, flexible, durable, and non-absorbent.

Figure 7:
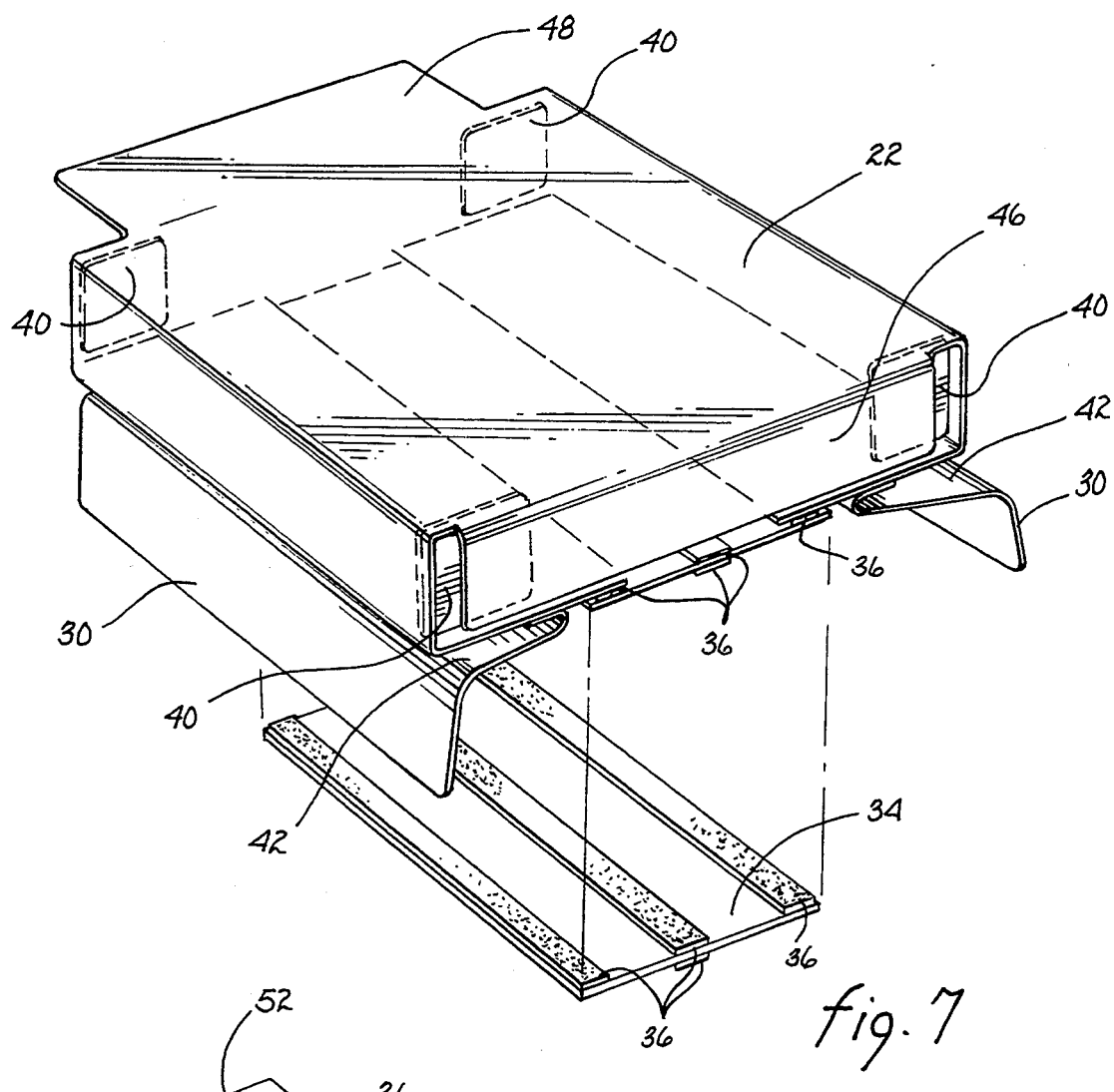
FIG. 7 is an exploded perspective view of the foot cushion from FIG. 1 and its associated protective cover showing the manner in which this portion of the surgical table protective cover is coupled to the foot cushion.

Referring to FIG. 7, the foot cushion protective cover 22 is shown with the connecting portion 34 aligned underneath the cover 22 in preparation for assembly, and the foot cushion protective cover 22 is also shown with the connecting portion 34 coupled to the cover 22. Each connection portion 34, and each protective cover 18, 20, and 22 with its associated cushion and table top 14 have a similar arrangement of the VELCRO sealing portions 36 in order to couple the protective covers 18, 20, and 22 to their respective cushions and to the surgical table top 14. The foot cushion protective cushion 22 has end flaps 46 and 48. Either of these flaps may be down like 46 or up like 48 depending upon the situation requirement.

Figure 8:
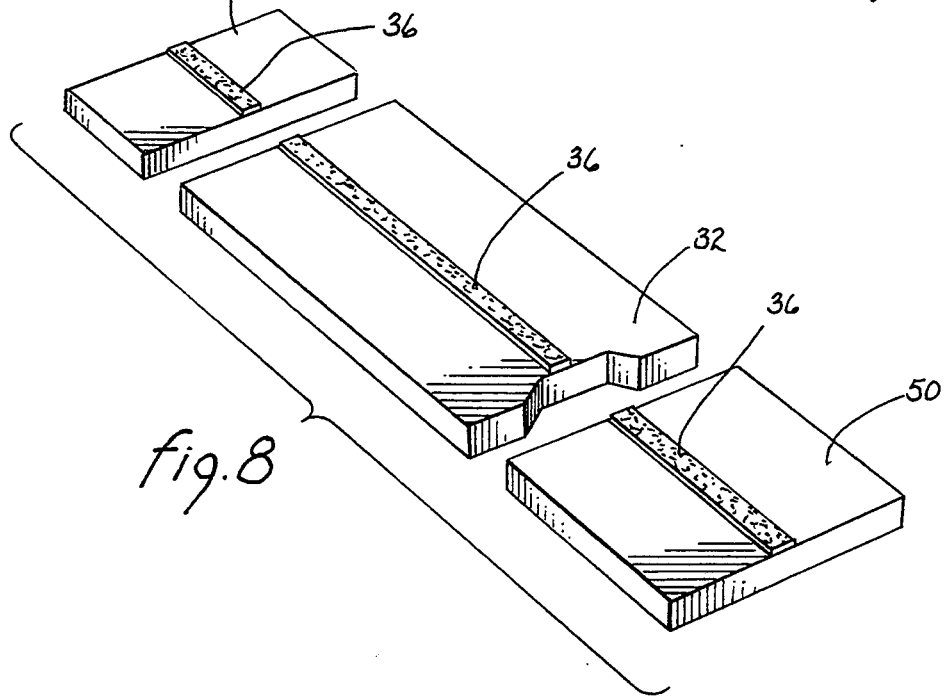
FIG. 8 is a perspective view showing the connection portions on the bottom portions of each of the head cushion, the mid-section cushion, and the foot cushion.

Referring to FIG. 8, the head cushion 52, the mid-section cushion 32, and the foot cushion 50 are shown with their VELCRO sealing portions 36 which are used to couple each of the cushions 52, 32, and 50 to their respective protective covers 18, 20, and 22 via connection portions 34.

OPERATION

Although different types of surgical tables and cushion arrangements can be used, for the purposes of discussing the basic operation, assume the use of a three-cushion arrangement of the type depicted in FIG. 1. The connection portions 34 are matched with their associated cushions 52, 32, and 50. The center VELCRO sealing portion 36 from the side of each of the connection portions 34 having three VELCRO sealing portions 36 is coupled to the corresponding VELCRO sealing portion 36 on the corresponding cushions 52, 32, and 50. The head cushion 52 is covered with the head cushion protective cover 18, and the head cushion protective cover's VELCRO sealing portions 36 are coupled to the corresponding VELCRO sealing portions 36 on the connection portion 34. In a similar manner, the mid-section cushion protective cover 20 and the foot cushion protective cover 22 are coupled to their respective cushions 32 and 50. The protected cushions 18, 20, and 22 are placed on their respective locations on the surgical table top 14, and the tucks and flaps are situated as desired. A bed sheet may be placed over the protective covers and tucked into place as previously described.

While the invention has been particularly shown and described with reference to the preferred embodiments thereof, it will be understood by those skilled in the art that the foregoing and other changes in form and details may be made therein without departing from the spirit and scope of the invention. For example, different types of surgical tables and different cushion arrangements can be accommodated. In addition, VELCRO sealing portions 36 could be used to hold various flaps in place, such as holding flap 24 in contact with the foot cushion protective cover 22.

I claim:

1. A combination surgical table and protective cover means comprising, in combination:

a surgical table having at least one cushion for supporting a patient; and protective cover means coupled to said cushion and to said surgical table for minimizing surface contamination of said cushion and said table comprising:

connecting means having a portion coupled to said table and having another portion coupled to said cushion for coupling said protective cover means to said cushion;

shielding means having a first portion and a second portion both coupled to said connecting means and having a general shape substantially equivalent to a shave of said cushion for shielding said cushion and said table from said contamination; and flow guide means coupled to said shielding means for directing said contamination away from both said cushion and said table.

2. The apparatus of claim 1 including a head cushion, a mid-section cushion, and a foot cushion for supporting a patient.

3. The apparatus of claim 2 wherein said mid-section cushion provides a perineal cut-out portion for perineal access.

4. The apparatus of claim 1 wherein said shielding means includes at least one flap.

5. The apparatus of claim 4 including a head cushion, a mid-section cushion, and a foot cushion for supporting a patient, said flap in a first position substantially covers any space between adjacent cushions.

6. The apparatus of claim 5 wherein said flap in a second position uncovers said space between adjacent cushions.

7. The apparatus of claim 6 wherein said space is a perineal access.

8. The apparatus of claim 1 wherein said flow guide means includes a first portion tucked between said cushion and said table and a second portion substantially extending away from between said cushion and said table.

9. The apparatus of claim 1 wherein each of said connecting means, said cushion, said table, and said shielding means includes VELCRO sealing means for coupling said connecting means to each of said table, said cushion, and said shielding means.

10. The apparatus of claim 1 wherein said protective cover means is substantially flexible and non-absorbent.

11. A method of operating a combination surgical table and protective cover means comprising the steps of:

providing a surgical table having at least one cushion for supporting a patient; and providing protective cover means coupled to said cushion and to said surgical table for minimizing surface contamination of said cushion and said table comprising the steps of:

providing connecting means having a portion coupled to said table and having another portion coupled to said cushion for coupling said protective cover means to said cushion;

providing shielding means having a first portion and a second portion both coupled to said connecting means and having a general shape substantially equivalent to a shape of said cushion for shielding said cushion and said table from said contamination; and providing flow guide means coupled to said shielding means for directing said contamination away from both said cushion and said table.

12. The method of claim 11 including a head cushion, a mid-section cushion, and a foot cushion for supporting a patient.

13. The method of claim 12 wherein said mid-section cushion provides a perineal cut-out portion for perineal access.

14. The method of claim 11 wherein said shielding means includes at least one flap.

15. The method of claim 14 including a head cushion, a mid-section cushion, and a foot cushion for supporting a patient, said flap in a first position substantially covers any space between adjacent cushions.

16. The method of claim 15 wherein said flap in a second position uncovers said space between adjacent cushions.

17. The method of claim 16 wherein said space is a perineal access.

18. The method of claim 11 wherein said flow guide means includes a first portion tucked between said cushion and said table and a second portion substantially extending away from between said cushion and said table.

19. The method of claim 11 wherein each of said connecting means, said cushion, said table, and said shielding means includes VELCRO sealing means for coupling said connecting means to each of said table, said cushion, and said shielding means.

20. The method of claim 11 wherein said protective cover means is substantially flexible and non-absorbent.

* * * * *